United States Patent [19]

Mikuni et al.

[11] Patent Number: 5,140,084
[45] Date of Patent: Aug. 18, 1992

[54] SILICON-CONTAINING ALPHA-CYANOACRYLATES

[75] Inventors: Hiroyuki Mikuni, Sagamihara; Toshiyuki Chikusa, Hachiohji, both of Japan

[73] Assignee: Three Bond Co., Ltd., Tokyo, Japan

[21] Appl. No.: 690,607

[22] Filed: Apr. 24, 1991

[30] Foreign Application Priority Data

Apr. 27, 1990 [JP] Japan .................. 65-110369
Apr. 27, 1990 [JP] Japan .................. 65-110370

[51] Int. Cl.$^5$ .............. C08F 30/08; C07F 7/10
[52] U.S. Cl. ........................... 526/279; 556/416
[58] Field of Search .................. 526/279; 556/416

[56] References Cited

FOREIGN PATENT DOCUMENTS 61-168607 7/1986 Japan .

Primary Examiner—Joseph L. Schofer
Assistant Examiner—Wu C. Cheng
Attorney, Agent, or Firm—Scully, Scott, Murphy & Presser

[57] ABSTRACT

A silicon-containing alpha-cyanoacrylate, useful as an adhesive, having the general formula:

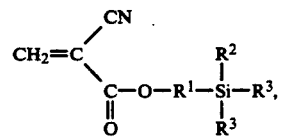

wherein $R^1$ is an alkylene group containing 1 to 6 carbon atoms; and $R^2$, $R^3$ and $R^4$ are each alkyl groups containing 1 to 6 carbon atoms, is disclosed. A process for preparing the silicon-containing alpha-cyanoacrylate compound is also set forth. In this process a cyanoacetate having the structural formula

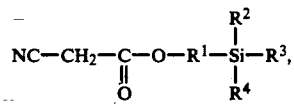

wherein $R^1$, $R^2$, $R^3$ and $R^4$ are as defined above, is dehydrocondensed with formaldehyde or paraformaldehyde in the presence of a basic catalyst to produce a condensation polymer. The condensation polymer is thereupon depolymerized at elevated temperature to produce the silicon-containing alpha-cyanoacrylate.

5 Claims, No Drawings

SILICON-CONTAINING ALPHA-CYANOACRYLATES

BACKGROUND OF THE INVENTION

The present invention relates to a novel α-cyanoacrylate and an adhesive containing same.

α-Cyanoacrylates represented by the following general formula polymerize and cure rapidly in the presence of water adsorbed on the surface of a material to be bonded and afford an adhesive force of an extremely high strength, so are widely used as room temperature one-pack type instantaneous adhesives for the bonding of metals, plastics, rubber and wood:

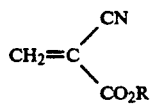

As α-cyanoacrylates there are known those with R being alkyl, such as alkyl α-cyanoacrylates, e.g. methyl α-cyanoacrylate, ethyl α-cyanoacrylate, and isopropyl α-cyanoacrylate, those with R being an unsaturated group, such as alkenyl or alkynyl α-cyanoacrylates, e.g. allyl α-cyanoacrylate and propargyl α-cyanoacrylate, fluoroalkyl α-cyanoacrylates (Japanese Patent Publication No. 87404/1982), e.g. 2,2,2-trifluoroethyl α-cyanoacrylate and 2,2,3,3-tetrafluoropropyl α-cyanoacrylate, and alkoxyalkyl α-cyanoacrylates, e.g. 2-methoxyethyl α-cyanoacrylate and 2-ethoxyethyl α-cyanoacrylate.

Generally, in the case where an α-cyanoacrylate is used as an adhesive, the cyanoacrylate monomer which has been volatilized polymerizes in the presence of water contained in the air and adheres as a white powder to the surrounding portion of a bonded part (whitening phenomenon), thus impairing the appearance of the bonded material. When used in the assembly of electric and electronic parts, the volatilized monomer contaminates a contact portion and causes defective contact, or cures in a moving part, thereby causing malfunction. Besides, many of α-cyanoacrylates have a stimulative odor. Further, cured polymers thereof are hard and deficient in flexibility, so are inferior in heat- and water-resistance.

It is the object of the present invention to overcome the above-mentioned drawbacks of the prior art.

SUMMARY OF THE INVENTION

In one aspect the present invention resides in a silicon-containing α-cyanoacrylate represented by the following general formula:

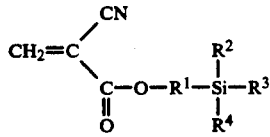

wherein $R^1$ is an alkylene group having 1 to 6 carbon atoms, and $R^2$ to $R^4$ are each an alkyl group having 1 to 6 carbon atoms.

The silicon-containing α-cyanoacrylate of the present invention can be prepared by a silicon-containing α-cyanoacetate represented by the following general formula:

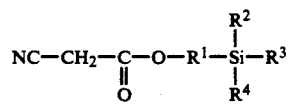

wherein $R^1$ to $R^4$ are as defined above, then dehydrocondensing this cyanoacetate with formaldehyde or paraformaldehyde in the presence of a basic catalyst, and depolymerizing (thermally decomposing) the resulting condensation polymer under heating.

In the silicon-containing α-cyanoacrylate of the present invention, $R^1$ to $R^4$ are not further restricted as long as the foregoing general formula is satisfied, but as examples of $R^1$ there are mentioned methylene, ethylene, propylene, and butylene, and as examples of $R^2$ to $R^4$ there are mentioned methyl, ethyl, propyl, and butyl.

The manufacturing process referred to above will be described below more concretely.

a. Preparation of Silicon-containing Cyanoacetate

A silicon-containing cyanoacetate represented by the general formula II can be prepared by an esterification reaction using cyanoacetic acid and a corresponding alcohol in the presence of 2-halopyridinium salt tertiary amine as a condensing agent in accordance with the following scheme:

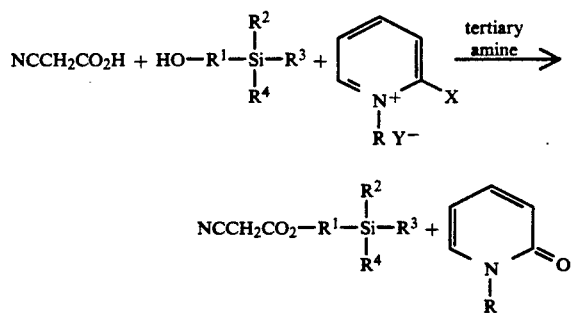

As examples of the 2-halopyridinium salt in the above reaction there are mentioned 2-chloro-1-methylpyridinium iodide (R=CH₃, X=Cl, Y=I), 2-bromo-1-methylpyridinium iodide (R=CH₃, X=Br, Y=I), 2-chloro-1-ethylpyridinium tetrafluoroborate (R=C₂H₅, X=Cl, Y=BF₄), and 2-bromo-1-ethylpyridinium tetrafluoroborate (R=C₂H₅, X=Br, Y=BF₄) As examples of the tertiary amine there are mentioned triethylamine, tributylamine, 2,6-lutidine, and pyridine.

The silicon-containing cyanoacetate can be prepared in high yield by utilizing the above reaction.

Conventional cyanoacetates are prepared by the following reaction using cyanoacetic acid and a corresponding alcohol in the presence of an acid catalyst:

However, this process is unsuitable for preparing the silicon-containing cyanoacetate used in the present invention. In the case of trimethylsilylethanol as an example, trimethylsilylethyl cation produced by acid does not react with cyanoacetic acid but is decomposed into trimethylsilyl cation and ethylene. Under the conventional conditions, therefore, the desired cyanoacetate is not produced.

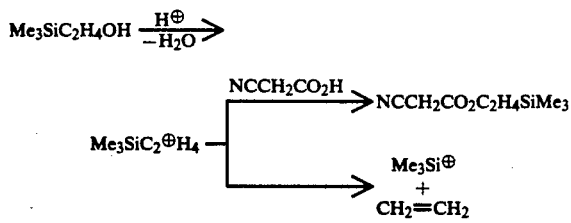

In the case of trimethylsilylmethanol, since the cation produced is a neopentyl type cation, the transition to a more stable tertiary cation is presumed.

When these points are taken into account, it can be said that the foregoing silicon-containing cyanoacrylate preparing process itself is a superior process.

b. Preparation of Silicon-containing Cyanoacrylate

The silicon-containing cyanoacetate prepared above is dehydrocondensed with formaldehyde or paraformaldehyde in the presence of a basic catalyst to obtain a condensation polymer.

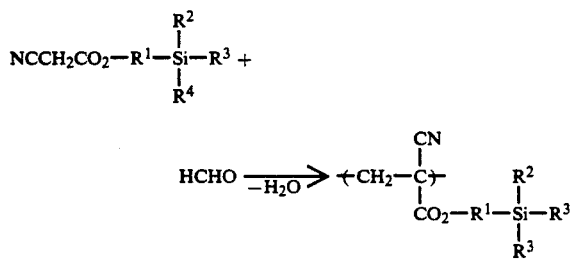

The condensation polymer thus obtained is then depolymerized at a temperature preferably of 140° to 250° C. under a reduced pressure, whereby there is obtained the silicon-containing α-cyanoacrylate of the present invention.

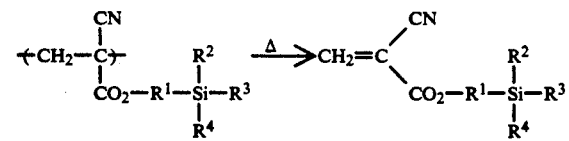

The silicon-containing α-cyanoacrylate thus obtained is very high in activity, so in order to preserve it stably it is desirable to add a stabilizer thereto. Examples of such stabilizer include, as anionic polymerization inhibitors, fulfurous acid ($SO_2$), sultone compounds, organic sulfonic acids, mercaptans, trifluoroacetic acid, and fluoroboric acid, and as radical polymerization inhibitors, quinones, catechol, pyrogallol, and 2,6-di-t-butylphenol. The amount of these stabilizers differs depending on the respective inhibiting abilities, but is preferably in the range of 1 to 10,000 ppm, more preferably 10 to 1,000 ppm, relative to the monomer.

The silicon-containing α-cyanoacrylate of the present invention is low in its vapor pressure so does not induce the whitening phenomenon when it cures. Besides, it emits scarcely any smell and so does not contaminate the working environment. Further, the silicon-containing α-cyanoacrylate of the invention possesses both the adhesive force peculiar to the α-cyanoacrylate and the characteristic feature of silicon atom, so it is employable not only as an adhesive but also as a coating agent.

In the second aspect the present invention resides in a cyanoacrylate-based adhesive containing a silicon-containing α-cyanoacrylate of the foregoing general formula I as an essential component.

In the silicon-containing α-cyanoacrylate used as an essential component in the invention, $R^1$ to $R^4$ are not further restricted as long as the general formula concerned is satisfied, but as examples of $R^1$ there are mentioned methylene, ethylene, propylene, and butylene, and as examples of $R^2$ to $R^4$ there are mentioned methy, ethyl, propyl, and butyl.

Examples of such silicon-containing α-cyanoacrylate in include trimethylsilyethyl α-cyanoacrylate, trimethylsilylpropyl α-cyanoacrylate, and dimethylethylsilylmethyl α-cyanoacrylate. These silicon-containing α-cyanoacrylates per se exhibit an excellent adhesive performance, high heat-and impact-resistance, and do not induce the whitening phenomenon. They may be used each alone as an adhesive, but if they are combined with conventional α-cyanoacrylates, the foregoing problems can be overcome effectively.

Such conventional α-cyanoacrylates are those represented by the following general formula:

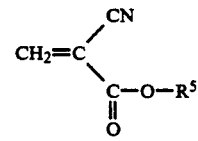

wherein $R^5$ is a hydrocarbon group such as alkyl, alkenyl, or alkynyl, or an alkoxy hydrocarbon group such as alkoxyalkyl. Examples are acrylate, ethyl α-cyanoacrylate, isopropyl α-cyanoacrylate, those wherein $R^5$ is alkoxyalkyl, e.g. 2-methoxyethyl α-cyanoacrylate and 2-ethoxyethyl α-cyanoacrylate, those wherein $R^5$ alkenyl, e.g. allyl α-cyanoacrylate, and those wherein $R^5$ is alkynyl, e.g. propargyl α-cyanoacrylate.

It is preferred that the silicon-containing α-cyanoacrylate be used in an amount of 5 wt % or more, more preferably 5 to 95 wt % based on the weight of an adhesive component.

The silicon-containing α-cyanoacrylate can be prepared by a thermal depolymerization of a dehydrocondensate obtained through the reaction in a suitable solvent, e.g. benzene-toluene, in the presence of a suitable basic catalyst.

In the cyanoacrylate-based adhesive composition according to the present invention there may be incorporated additives such as, for example, a radical polymerization inhibitor, an anionic polymerization inhibitor, a thickening agent, a filler, and a coloring agent.

The following examples are given to illustrate the present invention in more detail. The "part" and "%" in the following description are all by weight.

EXAMPLE 1

(Preparation of Silicon-containing α-Cyanoacetate)

8.5 g (0.1 mole) of cyanoacetic acid, 10.43 g (0.1 mole) of trimethylsilylmethanol, 30.66 g (0.12 mole) of 2-chloro-1-methylpyridinium iodide, 24.3 g (0.24 mole) of triethylamine and 200 ml of tetrahydrofuran were placed in a reaction vessel and reaction was allowed to take place at 50° C. for 3 hours in an argon atmosphere. Thereafter, a 10% aqueous sodium thiosulfate solution was added, followed by extraction with ether. An organic layer obtained was washed with a 10% aqueous sodium thiosulfate solution and then with water, then dried overnight with anhydrous magnesium. Thereafter, the desiccant was filtered off and the solvent was removed under a reduced pressure, followed by vacuum distillation to afford 14.6 g of trimethylsilylmethyl α-cyanoacetate ($NCCH_2CO_2CH_2SiMe_3$) (b.p. 81°-82° C./2 mmHg, yield 85%).

The following silicon-containing α-cyanoacetates were also prepared in the same way as above, whose yields and physical properties are also shown below:

Trimethylsilylethyl -cyanoacetate ($NCCH_2CO_2C_2H_4SiMe_3$)

Yield 83%, b.p. 94°-95° C./2 mmHg

Trimethylsilyl n-propyl α-cyanoacetate ($NCCH_2CO_2C_3H_6SiMe_3$)

Yield 82%, b.p. 94°-95° C./0.9 mmHg (Preparation of Silicon-containing α-Cyanoacrylate)

8.56 g (0.05 mole) of trimethylsilylmethyle α-cyanoacetate, 1.35 g (0.045 mole) of paraformaldehyde. 25.7 g of toluene and 8.6 mg of triethylenediamine were reacted together under reflux and water produced was removed by azeotropic dehydration. Then, 6.4 g of dioctyl phthalate, 87 mg of hydroquinone and 0.17 g of phophorus pentoxide were added and depolymerization was allowed to take place at 150°-210° C. under a reduced pressure to afford 3.86 g of crude trimethylsilylmethyl α-cyanoacrylate. Redistillation thereof afforded 2.48 g trimethylsilylmethyl α-cyanoacrylate (b.p. 67° C./2 mmHg, yield after purification 30%)

The following silicon-containing α-cyanoacrylates were also prepared in the same manner as above, whose physical properties are as shown below:

Trimethylsilylethyl α-cyanoacrylate

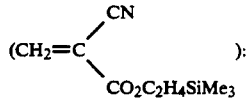

60MHz $^1$H-NMR [$CDCl_3$/$CHCl_3$ (δ = 7.24 ppm)]

δ(ppm): 6.92(s, 1H), 6.51(s, 1$^3$H), 4.44–4.16(m, 2H), 1.21–0.92(m, 2H), 0.94(s, 9H).

Trimethylsilyl n-propyl α-cyanoacrylate

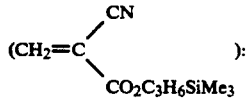

60MHz $^1$H-NMR [$CDCl_3$/$CHCl_3$ (δ = 7.24 ppm)]

-continued

δ(ppm): 6.91(s, 1H), 6.51(s, 1H), 4.15(t, J=7.0$H_z$, 2H), 1.96–1.46(m, 2H), 0.69–0.39(m, 2H), 0.06(s, 1H).

EXAMPLE 2

To check a whitening phenomenon, a schale which had been made clean was placed on black paper, and silicon-containing α-cyanoacrylates according to the present invention were each dropped one drop into the schale. After standing 24 hours at room temperature, the state of whitening was checked. For comparison, also as to conventional α-cyanoacrylates, the state of whitening was checked in the same manner. The results are as shown in Table 1 below.

TABLE 1

| Cyanoacrylate | Whitening |
|---|---|
| $CH_2=C\begin{smallmatrix}CN\\CO_2CH_3\end{smallmatrix}$ | x |
| $CH_2=C\begin{smallmatrix}CN\\CO_2CH_2CH=CH_2\end{smallmatrix}$ | x |
| $CH_2=C\begin{smallmatrix}CN\\CO_2C_2H_4OC_2H_4\end{smallmatrix}$ | Δ |
| $CH_2=C\begin{smallmatrix}CN\\CO_2CH_2SiMe_3\end{smallmatrix}$ | ° |
| $CH_2=C\begin{smallmatrix}CN\\CO_2C_2H_4SiMe_3\end{smallmatrix}$ | ° |
| $CH_2=C\begin{smallmatrix}CN\\CO_2C_3H_6SiMe_3\end{smallmatrix}$ | ° | x: whitened
Δ: slightly whitened
°: not whitened

EXAMPLE 3

Adhesives were prepared by mixing trimethylsilylmethyl α-cyanoacrylate (I) as a silicon-containing α-cyanoacrylate and ethyl α-cyanoacrylate (II) as a conventional α-cyanoacrylate in such proportions as shown in Table 2 below and then incorporating therein 20 ppm of $BF_3$ ethyl ether complex and 1000 ppm of hydroquinone. Their adhesive performances are as set forth in Table 2.

TABLE 2

| | (The mixing rations are all weight ratios.) | | | | |
|---|---|---|---|---|---|
| Mixing | Adhesive Performance (iron/iron) | | | | |
| Ratio (weight) (I)/(II) | Tensile Shear Strength (kgf/cm$^2$) | Hot Tensile Shear Strength (kgf/cm$^2$) | Impact Peel Strength (kgf · cm/cm$^2$) | Set Time (sec) | Property Whitening |
| 0/100 (comparative example) | 70 | 5 | 7.2 | 5 within | x |
| 20/80 | 80 | 4 | 8.2 | 15 within | Δ |

TABLE 2-continued (The mixing rations are all weight ratios.)

| Mixing Ratio (weight) (I)/(II) | Adhesive Performance (iron/iron) | | | Set Time (sec) | Property Whitening |
|---|---|---|---|---|---|
| | Tensile Shear Strength (kgf/cm$^2$) | Hot Tensile Shear Strength (kgf/cm$^2$) | Impact Peel Strength (kgf·cm/cm$^2$) | | |
| 40/60 | 75 | 5 | 7.6 | 15 within | Δ |
| 60/40 | 90 | 6 | 9.3 | 20 within | ○ |
| 80/20 | 90 | 14 | 9.1 | 20 within | ○ |
| 100/0 | 75 | 28 | 9.2 | 30 within | ○ |

EXAMPLE 4

Adhesives were prepared by mixing trimethylsilylmethyl α-cyanoacrylate (I) as a silicon-containing α-cyanoacrylate and allyl α-cyanoacrylate (III) as a conventional α-cyanoacrylate in such proportions as shown in Table 3 below and then incorporating therein 20 ppm of BF$_3$ ethyl ether complex and 1000 ppm of hydroquinone. Their adhesive performances are as set forth in Table 3.

TABLE 3

| Mixing Ratio (weight) (I)/(II) | Adhesive Performance (Fe/Fe) | | | Set Time (sec) | Property Whitening |
|---|---|---|---|---|---|
| | Tensile Shear Strength (kgf/cm$^2$) | Hot Tensile Shear Strength (kgf/cm$^2$) | Impact Peel Strength (kgf·cm/cm$^2$) | | |
| 0/100 (comparative example) | 100 | 5 | 10.3 | <5 | x |
| 20/80 | 100 | 13 | 10.5 | <5 | Δ |
| 40/60 | 85 | 12 | 10.2 | <15 | ○ |
| 60/40 | 90 | 16 | 12.3 | <20 | ○ |
| 80/20 | 90 | 26 | 13.8 | <20 | ○ |
| 100/0 | 75 | 28 | 9.2 | <30 | ○ |

EXAMPLE 5

An adhesive was prepared by mixing trimethylsilylethyl α-cyanoacrylate (IV) as a silicon-containing cyanoacrylate and ethyl α-cyanoacrylate (II) as a conventional -cyanoacrylate at a ratio of 80:20 and incorporating therein 20 ppm of BF$_3$ ethyl ether complex and 1000 ppm of hydroquinone. Its adhesive performance is as shown in Table 4.

EXAMPLE 6

An adhesive was prepared by mixing trimethylsilylpropyl α-cyanoacrylate (V) as a silicon-containing cyanoacrylate and ethyl α-cyanoacrylate (II) as a conventional α-cyanoacrylate at a ratio of 80:20 and incorporating therein 20 ppm of BF$_3$ ethyl ether complex and 1000 ppm of hydroquinone. Its adhesive performance is as shown in Table 4.

TABLE 4

$$CH_2=C(CN)-C(=O)-O-R-Si(CH_3)_3 :$$

$$CH_2=C(CN)-C(=O)-O-C_2H_5 =$$

80:20

| | Adhesive Performance | | | | |
|---|---|---|---|---|---|
| | Tensile Shear Strength (kgf/cm$^2$) | Hot Tensile Shear Strength (kgf/cm$^2$) | Impact Peel Strength (kgf·cm/cm) | Set Time | Property Whitening |
| R = CH$_2$ | 90 | 14 | 9.1 | <20 | ○ |
| R = C$_2$H$_4$ | 80 | 16 | 10.0 | <30 | ○ |
| R = C$_3$H$_6$ | 75 | 19 | 10.5 | <30 | ○ |
| $CH_2=C(CN)-C(=O)-O-C_2-H_5$ (100% comparative example) | 70 | 5 | 7.2 | <5 | x |

Testing Methods

Tensile Shear Strength:

Measured at 25° C. after curing 24 hours at 25°±1° C., 60±2% RH, according to JIS K6861-1977.

Hot Tensile Shear Strength:

Measured at 150° C. in 150° C.×1 hr after curing 24 hours at 25°±1° C., 60±2% RH, according to JIS K6861-1977.

Impact Peel Strength:

Measured at 25° C. after curing 24 hours at 25°±1° C., 60±2% RH, according to JIS K6854-1977.

Set Time:

Measured at 25°±1° C., 60±2% RH, according to JIS K6861-1977.

Whitening:

A schale which had been made clean was placed on black paper, and each adhesive was dropped one drop into the schale. After standing 24 hours at 25° C., 60% RH, the presence or the state of whitening was checked.

EXAMPLE 7

Adhesives were prepared by mixing trimethylsilylmethyl α-cyanoacrylate (I), trimethylsilylethyl α-cyanoacrylate (IV) and trimethylsilylpropyl α-cyanoacrylate, as silicon-containing cyanoacrylates, and 2-ethoxyethyl α-cyanoacrylate (VI) as a conventional α-cyanoacrylate, at a ratio of the former to the latter of 80:20 (weight ratio), and then incorporating therein 20 ppm of BF$_3$ ethyl ether complex and 1000 ppm of hydroquinone. Their adhesive performances are as shown in Table 5.

3. An adhesive composition as set forth in claim 2, further containing a conventional α-cyanoacrylate represented by the following general formula:

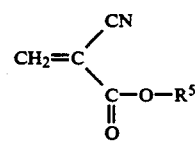

wherein R$^5$ is a hydrocarbon group or an alkoxyhydrocarbon group.

4. An adhesive composition as set forth in claim 3, wherein said silicon-containing α-cyanoacrylate is pres-

TABLE 5

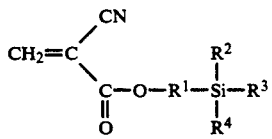

| | Adhesive Performance | | | | |
|---|---|---|---|---|---|
| 80:20 | Tensile Shear Strength (kgf/cm$^2$) | Hot Tensile Shear Strength (kgf/cm$^2$) | Impact Strength (kgf·cm/cm$^2$) | Set Time (sec) | Property Whitening |
| R = CH$_3$ | 85 | 20 | 10.6 | <30 | ○ |
| R = C$_2$H$_4$ | 85 | 22 | 10.9 | <45 | ○ |
| R = C$_3$H$_6$ | 75 | 23 | 11.3 | <50 | ○ |
| 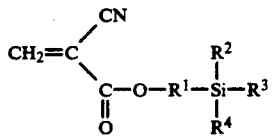 | 70 | 5 | 7.2 | <20 | △ |

(100% comparative example)

What is claimed is:

1. A silicon-containing α-cyanoacrylate represented by the following general formula:

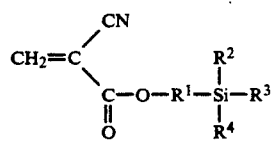

wherein R$^1$ is an alkylene group having 1 to 6 carbon atoms, and R$^2$ to R$^4$ are each an alkyl group having 1 to 6 carbon atoms.

2. A cyanoacrylate-based adhesive composition containing as an essential component a silicon-containing α-cyanoacrylate represented by the following general formula:

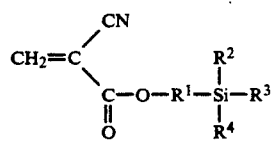

wherein R$^1$ is an alkylene group having 1 to 6 carbon atoms, and R$^2$ to R$^4$ are each an alkyl group having 1 to 6 carbon atoms.

ent in an amount of 5 to 95% by weight based on the total cyanoacrylate weight.

5. A process for preparing a silicon-containing α-cyanoacrylate represented by the structural formula

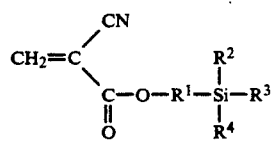

wherein R$^1$ is an alkylene group having 1 to 6 carbon atoms; and R$^2$ to R$^4$ are each an alkyl group having 1 to 6 carbon atoms, said process comprising dehydrocondensing a cyanoacetate having the structural formula

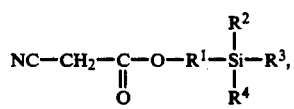

wherein R$^1$ is an alkylene group having 1 to 6 carbon groups; and R$^2$ to R$^4$ are each an alkyl group having 1 to 6 carbon groups, with formaldehyde or paraformaldehyde in the presence of a basic catalyst wherein a condensation polymer is formed; and depolymerizing said condensation polymer at elevated temperature.

* * * * *